Figure 1:
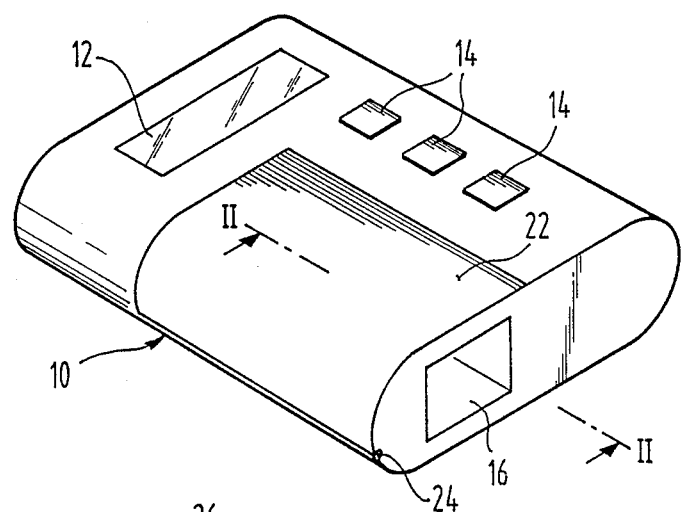

United States Patent [19]

Gassenhuber

[11] Patent Number: 4,934,817
[45] Date of Patent: Jun. 19, 1990

[54] DEVICE WITH DETACHABLE TEST STRIP HOLDER FOR OPTICALLY EVALUATING A TEST STRIP

[75] Inventor: Helmut Gassenhuber, Starnberg, Fed. Rep. of Germany

[73] Assignee: LRE Relais+Elektronik GmbH, Munich, Fed. Rep. of Germany

[21] Appl. No.: 280,696

[22] Filed: Dec. 6, 1988

[30] Foreign Application Priority Data

Dec. 9, 1987 [DE] Fed. Rep. of Germany ....... 8716270

[51] Int. Cl.$^5$ ..................... G01N 21/47; G01N 21/01
[52] U.S. Cl. .................................... 356/446; 356/244; 422/68.1
[58] Field of Search .................. 356/446, 244; 422/68, 422/58

[56] References Cited

U.S. PATENT DOCUMENTS

| | | | |
|---|---|---|---|
| 4,372,682 | 2/1983 | Nenninger et al. | 356/244 |
| 4,509,859 | 4/1985 | Markart et al. | 356/446 |
| 4,780,283 | 10/1988 | Meinecke et al. | 422/68 |

Primary Examiner—Vincent P. McGraw

[57] ABSTRACT

A device for optically evaluating test strips includes a housing carrying the measuring optics and a test strip holder insertable into and removable from the housing by sliding into and out of a receiving compartment of the housing, with the test strip holder containing all of the surfaces with which the significant portions of test strips come into contact, thereby permitting those surfaces to be easily cleaned upon removal of the test strip holder from the housing. The device also assures proper positioning of an easily inserted test strip, allows for heating of the test field to a fixed temperature, and allows for both empty and dark field calibration of the optical system.

11 Claims, 2 Drawing Sheets

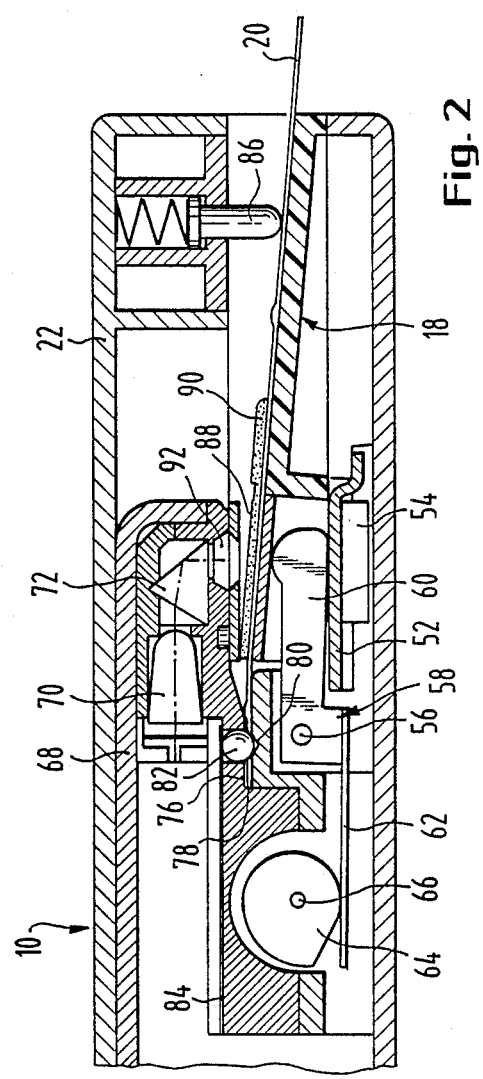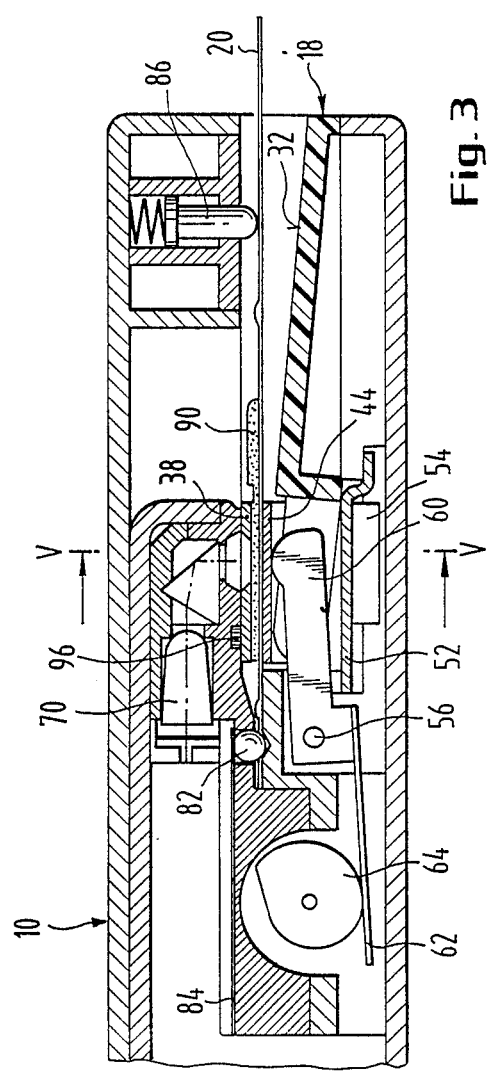

DEVICE WITH DETACHABLE TEST STRIP HOLDER FOR OPTICALLY EVALUATING A TEST STRIP

The invention concerns a device for optically evaluating a test strip having a least one test field, the device including a housing with a receiving compartment for the test strip, and a measuring optical system with a sender for illuminating the test field, a receiver for receiving light remitted from the test field and an electronic evaluating and indicating means. The device is especially intended for testing the cholesterol content of blood.

A dependable measurement using the previously mentioned device requires that the measuring apparatus not be dirtied by previous measurements and that the test strip always take a definite position relative to the measuring optical system.

The invention has as its object the construction of a device of the aforegoing type so that all components of it which come into contact with the test strips can be easily cleaned and so that a precise placement of the test strips relative to the measuring optical system is assured.

This object is achieved in accordance with the invention by a test strip holder releasably insertable into the receiving compartment with a receiving groove for the test strip, the width of which groove along at least part of its length corresponds to the width of the test strip, a support plate arranged in spaced relation to the groove bottom of the test strip holder and having a measuring opening, a pressing element moveably supported in the receiving groove below the support plate and which is movable between a first position in which it is essentially aligned with the groove bottom and a second position in which it presses the test strip to the support plate, and a mechanism for moving the pressing element between its first and second positions.

In the case of the solution provided by the invention, the parts of the test strip which provide the liquid under investigation and the reaction substance engage only the test strip holder and the parts arranged on it. The test strip holder can moreover be entirely removed from the device and thereby can be easily cleaned so that the measurements are not influenced by dirtiness remaining from previous measurements. As a result of the pressing of the test strip to the support plate, a definite positioning of the test strip relative to the measuring optical system is simultaneously guaranteed. It is also possible by pressing the pressing element without a test strip to close the measuring opening of the support plate and thereby perform a dark calibration of the device. Further, by opening the housing of the device with an inserted test strip, the liquid to be investigated can be applied to the receiving field of the test strip without the test strip having to have its position changed again. It is also possible to perform an empty calibration, that is a comparison measurement under identical measuring conditions on the test strip, without the substance to be investigated dropped onto it.

In order to assure the test strip not only against lateral shifting, but also against shifting in its longitudinal direction, it is expedient if a stop for the test strip is provided near the inner end of the receiving compartment and inside of the device as well as if a clamping device is provided for forcibly holding the test strip fixed in its inserted condition.

Advantageously, the bottom of the receiving groove rises from its input end inwardly to the support plate. If the test strip is inserted only in the receiving groove but not pressed against the support plate there exists in this position of the test strip the possibility of aerating the test field. This can be prevented if a pressing pin is moveably supported in a housing cover covering the receiving compartment near the input end of the receiving compartment and biased in the direction toward the groove bottom of the test strip holder, which pressing pin presses the test strip against the groove bottom so long as the test strip is not pressed by the pressing device against the support plate.

In order to obtain temperature-wise similar measuring conditions for all measurements, the invention provides that the support plate and the pressing element are heating by means of a regulatable heating device. Since the test field is clamped between the support plate and the pressing element, its temperature is determined by the temperature of these two components since the test strip in this region has practically no heat contact with the surroundings.

According to a preferred embodiment, the support plate is formed as the cross-piece of a U-shaped support component whose U-legs point toward the groove bottom. The pressure element likewise has a U-shaped cross section and is arranged parallel to the support component between its U-legs, the U-legs of the pressing element being spaced from the U-legs of the support component. Finally a U-shaped heating element carrier is provided, on whose cross-piece a heating element is arranged and whose U-legs are enclosed between the U-legs of the pressing element and of the support component. The heating element carrier is thereby fixed to the housing. Especially if the support component and the pressing element are made of a good heat conducting material, preferably metal, the heat energy of the heating element can be well transferred to these components. The test strip holder is moreover preferably made of plastic since this material can easily be cleaned and moreover possesses good thermal insulating properties.

Figure 4:
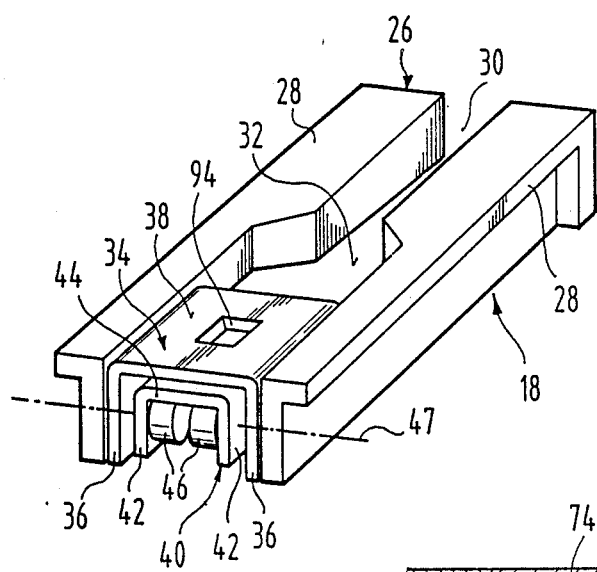
Figure 5:
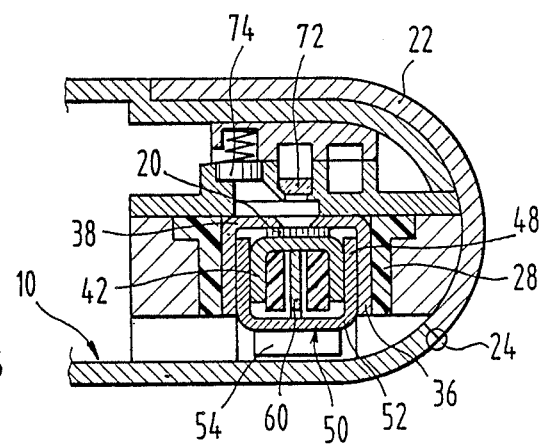

Further features and advantages of the invention will be apparent from the further dependent claims and the following description, which in connection with the accompanying drawings explain the invention with respect to an exemplary embodiment. The drawings show:

FIG. 1 - a schematic total view of a measuring device according to the invention, FIG. 2 - a partially schematic cross sectional view through the device along the line II—II of FIG. 1, with a test strip being shown inserted in the device, FIG. 3 - a view corresponding to FIG. 2 with an inserted test strip pressed to the measuring optical system, FIG. 4 - a schematic, perspective representation of the test strip holder alone, and FIG. 5 - a partial view through the device along the line V—V of FIG. 3.

The device illustrated in FIG. 1 serves, for example, for testing the cholesterol content of blood by the measurement of remitted light using a measuring optical system in the device. The device includes a housing, indicated generally at 10, on whose upper side are an indicating means 12 and operating elements 14. The indicating means 12 and the operating elements 14 are only schematically represented. They do not necessarily agree in number and arrangement with the arrangement found in an actual device. For the explanation of the present invention their arrangement plays no role. On the end of the device facing the observer is a receiving compartment 16 for receiving a test strip holder 18, illustrated in FIG. 4, in which a test strip 20 can be inserted in a still to be described way (FIGS. 2 and 3). Above the receiving compartment 16 is a hinged cover 22 in the housing 10, which cover can be pivoted about an axis 24 to give access to a drop applying field on the test strip 20 lying in the test strip holder 18, as is explained in more detail in connection with FIGS. 2 and 3.

The test strip holder (18) illustrated in FIG. 4 includes a one-piece plastic part 26 with two lateral profiled legs 28 which embrace between them a receiving groove 30 for receiving a test strip 20, with the groove bottom 32 as illustrated in FIGS. 2 and 3 sloping upwardly from the inlet end of the test strip holder 18 to its other longitudinal end which faces the inside of the housing. The groove bottom 32 therefore forms a ramp on which the test strip 20 can be inserted into the device. The width of the end section of the receiving groove 30 directly at the input end in general corresponds to the width of the test strip 20 so that the test strip is laterally guided.

A U-shaped support part 34 is fixedly arranged between the free ends of the profiled legs 28 at the longitudinal end of the test strip holder 18 facing the interior of the device. The U-shaped legs 36 of the support part are positioned adjacent the neighboring profiled legs 28 and the cross piece 38 of the support part forms a support plate aligned with the upper edges of the profile legs 28. The support part 34 is rigidly connected with the plastic part 26.

A U-shaped pressing element 40 is arranged inside of the U-shaped support part 34 and is arranged with its U-legs 42 and its cross piece 44 in essentially parallel relationship to the corresponding parts of the support part 34, from which it however is spaced. The pressing element 40 is supported for pivotal movement about an axis 47 on extensions 46 of the plastic part 26, as shown in FIG. 4, so that in a first position it aligns with the ramp forming groove bottom 32 (FIG. 2) suitably for receiving a test strip 20 and, in a second position, corresponding to the pressed position of the test strip 20 against the support plate 38 lies parallel to the support plate 38 (FIG. 3). The pressing element 40 is preferably made of metal.

If the test strip holder 18 is inserted into the receiving compartment 16 of the housing 10 (FIGS. 2, 3 and 5), there is received between the U-legs 36 and 42 of the support part 34 and of the pressing element 40 the U-legs 48 of a U-shaped heating element carrier 50 arranged below the receiving compartment 16 in the housing 10 and carrying a heating element 54 on the side of its cross piece 52 remote from the test strip holder 18. By heat conduction and radiation, the heating element carrier transfers heat to the pressing element 40 and to the support part 34.

A two-armed pressing lever 58 is pivotally supported for movement about an axis 56 near the inner end of the receiving compartment 16. It lies, as to its one lever arm 60, between the extensions 46 under the cross piece 44 of the pressing element 40. Its opposite lever arm is formed by a leaf spring 62 which lies against the periphery of a cam 64 supported in the housing 10 for movement about an axis 66.

Above the receiving compartment 16, in an inner housing 68, is a measuring optical system for carrying out the measurement of remitted light, the system having a sender 70, a bending prism 72 and a receiver 74 (FIG. 5).

Further, near the inner end of the receiving compartment is a slot 76 located between two surfaces fixed relative to the housing and extending along the length of the receiving groove 30, the end surface 78 of the slot forming a stop surface for the input end of the test strip 20 when the strip is inserted into the receiving compartment or into the receiving groove of the test strip holder 18. In the inserted position (FIGS. 2 and 3) the test strip is forcibly held in place by a clamping apparatus which includes a notch 80 in the surface bordering the slot 76 and a detent ball 82, associated with the notch 80, in the other surface bordering the slot with the detent ball 82 being biased, for example by a leaf spring 84, in the direction toward the notch 80.

The test strip 20, which as shown in FIG. 2 is inserted to the stop surface 78, lies flat on the groove bottom 32 and is held against the groove bottom 32 by a pressing pin 86 spring supported in the housing cover 22. The measurements are so chosen that a test field 88 of the test strip 20 is positioned exactly between the support plate 38 and the cross-piece 44 of the pressing element 40 when the test strip 20 is completely inserted. The drop applying field 90 connected with the test field 80 therefore lies free. For carrying out a measurement the cam 64 is turned from the position illustrated in FIG. 2 to the position illustrated in FIG. 3, as a result of which the pressing lever 58 is pivoted counter-clockwise and causes the cross-piece 44 of the pressing element 40, along with the test strip 20, to be pressed flat against the underside of the support plate 38. The test field 88 therefore becomes located in a well-defined position relative to the measuring optical system 70, 72 and 74. The ray path from the sender 70 passes through the prism 72 and an opening 92 in the optics receiving housing as well as through a window 94 in the support plate 38 to the test field 88 from which rays are remitted back to the receiver 74. If no test strip 20 is inserted, and the window 94 is closed by pressing of the pressing element 40, a dark calibration of the device can be made. Further, after the pressing of the test strip 20 (FIG. 3) an empty calibration can next take place before the liquid to be investigated is dropped onto the drop applying field 90. The drop application field in this instance is freely accessible through the opening of the cover 22. While the reaction takes place, which occurs after the dropping on of the liquid to be investigated but before the measurement of the test field 88, this area of the test strip 20 is held at a predetermined temperature by the heating apparatus 50, 54. In connection with this, a temperature sensor 96 is used which in the inserted condition of the test strip holder 18, comes into engagement with the support plate 38, the sensor being operatively connected with a non-illustrated regulating device which maintains a constant pre-given temperature. If the test field is to be aerated, the pressing lever is set back from the position illustrated in FIG. 3 to the position illustrated in FIG. 2 through rotation of the cam 64, as a result of which the pin 86 presses the test strip 20 against the groove bottom 32 and therefore serves to release the test field 88 from the support plate 38. In this condition, the test strip 20 can also be removed from the device.

The aforegoing description shows that all of the surfaces which come into engagement with the test field 88 and with the drop application field 90 of the test strip 20 are arranged on the test strip holder 18, which can be taken from the device 10 and subsequently easily cleaned. Only the forward end of the test strip which projects beyond the test field 88 comes into contact with parts inside of the device, but a dirtying of this area cannot have any influence on the measurement results. The test strip can be brought in a simple way into a definite position which always remains the same for the measurement, and at the same time, its temperature can be held at a predetermined stabilized value. In connection with the easy possibility for a dark calibration of the measuring apparatus and for an empty calibration, the previously described arrangement of the invention permits the carrying out of exact and reproducible measurements.

We claim:

1. A device for optically evaluating at least a test field (88) of a test strip (20), including a housing (10) with a receiving compartment (16) for the test strip (20), a measuring optical system (70, 72, 74) with a sender (70) for illuminating the test field (88), a receiver (74) for receiving light remitted from the test field (88) and an electronic evaluating and indicating device, characterized by a test strip holder (18) releasably insertable in the receiving compartment (16) with a receiving groove (30), for the test strip (20), whose width corresponds to the width of the test strip (20) over at least a portion of its length, a support plate (38) arranged on the test strip holder (18) in spaced relation to the groove bottom (32) and having a measuring opening (94), a moveably supported pressing element 40 moveable in the receiving groove (30) below the support plate (38), which pressing element is moveable between a first position in which it is generally aligned with the groove bottom (32) and a second position in which it presses the test strip (20) onto the support plate (38), and a pressing device (58, 64) for adjusting the pressing element (40) between its first and second positions.

2. A device according to claim 1 further characterized in that near the inner end of the receiving compartment is a stop (78) for the test strip (20) as well as a clamping device (80, 82) for forcibly holding the test strip (20) in its inserted condition.

3. A device according to claim 1, further characterized in that the bottom (32) of the receiving groove (30) inclines upwardly from its input end to the support plate (38).

4. A device according to claim 1, further characterized in that the support plate (38) and the pressing element (40) are heatable by a regulatable heating apparatus (50, 54, 96).

5. A device according to claim 4, further characterized in that the support plate (38) is formed by the cross-piece of a U-shaped support component (34) whose U-legs (36) are directed away from the groove bottom (32), that the pressing element (40) has a U-shaped cross section and is arranged parallel to the support part (34) between its U-legs (36), the U-legs (42) of the pressing element (40) having a spacing from the U-legs of the support part (34), and that a U-shaped heating element carrier (50) is provided on whose cross-piece (52) a heating element (54) is arranged and whose U-legs (48) are received between the U-legs (42 and 36) of the pressing element (40) and the support part (34).

6. A device according to claim 5, further characterized in that the support part (34) and the pressing element (40) are made of good heat conducting material.

7. A device according to claim 1 further characterized in that the pressing device includes a two-armed pivoting lever (58) which with its one lever end (60) lies on the side of the pressing element (40) facing away from the test strip (20) and which through a cam (64) at its other lever end (62) is adjustable between a pressing position and a releasing position.

8. A device according to claim 7, further characterized in that the lever arms (62, 60) are made as spring legs.

9. A device according to claim 7, further characterized in that the cam (64) is adjustable by a drive motor.

10. A device according to claim 1, further characterized by a housing cover (22) covering the receiving compartment (16), and in that a biased pressing pin (86) is supported near the input end of the receiving compartment (16) and is biased in the direction toward the groove bottom (32) of the test strip holder (18).

11. A device according to claim 1, further characterized in that the test strip holder is made of plastic.

* * * * *